US005340811A

United States Patent [19]

Kajihara et al.

[11] Patent Number: 5,340,811

[45] Date of Patent: * Aug. 23, 1994

[54] ISOQUINOLINE-OR QUINOLINE-SULFONAMIDE DERIVATIVE AND A PHARMACEUTICAL COMPOSITION COMPRISING THE SAME

[75] Inventors: Akiro Kajihara, Nobeoka; Shiro Miyoshi, Kashiwa, both of Japan

[73] Assignee: Asahi Kasei Kogyo Kabushiki Kaisha, Osaka, Japan

[ * ] Notice: The portion of the term of this patent subsequent to Dec. 24, 2002 has been disclaimed.

[21] Appl. No.: 536,630

[22] Filed: Jul. 17, 1990

[51] Int. Cl.[5] .......... C07O 401/12

[52] U.S. Cl. .......... 514/253; 540/553; 540/575; 544/363; 546/140; 546/141; 546/178; 514/218; 514/387; 514/309; 514/311

[58] Field of Search .......... 544/363; 514/253

[56] References Cited

U.S. PATENT DOCUMENTS

| | | | |
|---|---|---|---|
| 4,456,757 | 6/1984 | Hidaka et al. | 544/363 |
| 4,525,589 | 6/1985 | Hidaka et al. | 544/363 |
| 4,560,755 | 12/1985 | Hidaka et al. | 544/363 |
| 4,634,770 | 1/1987 | Hidaka et al. | 544/363 |
| 4,678,783 | 7/1987 | Hidaka et al. | 544/363 |
| 4,709,032 | 11/1987 | Hidaka et al. | 544/363 |
| 4,798,897 | 1/1989 | Hidaka et al. | 546/139 |
| 5,081,244 | 1/1992 | Hidaka et al. | 544/363 |
| 5,081,246 | 1/1992 | Hidaka et al. | 544/363 |
| 5,244,895 | 9/1993 | Hidaka et al. | 544/363 |
| 5,245,034 | 9/1993 | Hidaka et al. | 544/363 |

FOREIGN PATENT DOCUMENTS

| | | |
|---|---|---|
| 0109023 | 5/1984 | European Pat. Off. . |
| 61-126026 | 6/1986 | Japan . |
| 61-271221 | 12/1986 | Japan . |
| 61-293914 | 12/1986 | Japan . |
| 63-211267 | 9/1988 | Japan . |
| 2-73067 | 3/1990 | Japan . |
| 66-13875 | 9/1991 | PCT Int'l Appl. . |

OTHER PUBLICATIONS

Journal of Medicinal Chemistry, vol. 32, pp. 42–46, "5-Isoquinoline-sulfonamide Derivatives. . . . ", Anri Morikawa et al. (1989).

Agents and Actions, vol. 28 (3–4), pp. 173–184, "The Effect of Leukotriene Antagonists, Lipoxygenase . . . ", W. Kreutner et al. (1989).

Pharmacology, vol. 37 (3), pp. 187–194, "Antibroncho-constrictor Activity of the Intracellular Calcium . . . ", R. Chapman et al. (1988).

Morikawa et al, Jour Med Chem vol 32 pp. 46–50 (1989).

Phosphorus and Sulfur, 1988, vol. 40, A. Hafez et al., pp. 219–225.

R. M. Acheson, *Chemistry of Heterocyclic Compounds*, 3d ed. (Tokyo, Kagaku Gijitsu Shuppansha, 1980), pp. 322–324.

*Primary Examiner*—Donald G. Daus

*Attorney, Agent, or Firm*—Finnegan, Henderson, Farabow, Garrett & Dunner

[57] ABSTRACT

Disclosed is a sulfonamide derivative represented by following formula (I) and a medicine for the treatment of asthma comprising the sulfonamide derivative as an active ingredient which exhibits bronchodilation effect.

$$X-SO_2\!\left(NHCH_2\overset{R^3}{\overset{|}{C}}H\right)_{n}R^4 \qquad (I)$$

wherein X represents a quinoline residue represented by formula (II) or an isoquinoline residue represented by formula (III)

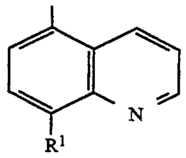

(II)

where $R^1$ is a hydrogen atom, a halogen atom, a lower alkyl group or a lower alkoxy group, or (Abstract continued on next page.)

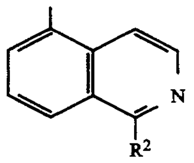

(III)

where $R^2$ is a hydrogen atom or a hydroxyl group, and wherein:

when X is quinoline residue (II), n is zero or 1, in which, when n is zero, $R^4$ is an unsubstituted or substituted diazacycloalkyl group, and when n is 1, $R^3$ is a hydrogen atom or a lower alkyl group and $R^4$ is an unsubstituted or substituted aralkylamino group or an unsubstituted or substituted diazacycloalkyl group; and when X is isoquinoline residue (III), n is 1, in which, $R^3$ is a hydrogen atom or a lower alkyl group and $R^4$ is a 3,4-methylenedioxyphenethylamino group, a 3,4-methylenedioxybenzylamino group or an unsubstituted or substituted diazacycloalkyl group, with the proviso that when $R^4$ is an unsubstituted or substituted diazacycloalkyl group, the diazacycloalkyl group is bonded at a nitrogen atom thereof.

13 Claims, No Drawings

ISOQUINOLINE-OR QUINOLINE-SULFONAMIDE DERIVATIVE AND A PHARMACEUTICAL COMPOSITION COMPRISING THE SAME

DESCRIPTION

Technical Field

The present invention relates to a novel sulfonamide derivative and a pharmaceutical composition comprising the same. More particularly, the present invention is concerned with a sulfonamide derivative which contains an unsubstituted or substituted diazacycloalkyl group or an unsubstituted or substituted aralkylamino group and is substituted with a quinoline residue or an isoquinoline residue, or an acid addition salt thereof. The sulfonamide derivative or an acid addition salt thereof of the present invention affects the bronchial smooth muscle of a mammal and is effective as an active ingredient of a pharmaceutical composition for the prevention and treatment of respiratory diseases, such as asthma. The present invention also relates to a pharmaceutical composition comprising the above-mentioned novel sulfonamide derivative or an acid addition salt thereof as an active ingredient.

Background Art

Various compounds have been proposed as a drug for treatment of respiratory diseases, particularly as a drug for treatment of peripheral circulatory disorders, cerebral circulation disorders, angina and the like. In this connection, reference may be made to, for example, European Patent No. 0061673 (U.S. Pat. Nos. 4,456,757, 4,560,755, 4,525,589, Japanese Patent Application Laid-Open Specification No. 57-156463, Japanese Patent Application Laid-Open Specification No. 57-200366, Japanese Patent Application Laid-Open Specification No. 58-121278, Japanese Patent Application Laid-Open Specification No. 58-121279), European Patent No. 0109023 (U.S. Pat Nos. 4,634,770, 4,709,023, Japanese Patent Application Laid-Open Specification No. 59-93054, Japanese Patent Application Laid-Open Specification No. 60-81168), U.S. Pat. No. 4,678,783 (Japanese Patent Application Laid-Open Specification No. 61-152658, Japanese Patent Application Laid-Open Specification No. 61-227581), U.S. Pat. No. 4,798,897 (Japanese Patent Application Laid-Open Specification No. 62-103066, Japanese Patent Application Laid-Open Specification No. 62-111981), Journal of Medicinal Chemistry, 32, 42–50 (1989) , Agents Actions, 28 (3–4) , 173–184 (1989) and Pharmacology, 37 (3), 187–194 (1988).

It is known that N-(2-aminoethyl)-N-hexyl-5-isoquinolinesulfonamide, 1-(5-isoquinolinesulfonyl)-3-aminopiperidine and the like described in U.S. Pat. No. 4,798,897, and N-(2-guanidinoethyl)-5-isoquinolinesulfonamide described in Agents Actions, 28 (3–4), 173–184 (1989), Pharmacology, 37 (3), 187–194 (1988) and European Patent No. 0109023 have not only vasodiletic activity but also bronchodilating activity. However, the bronchodilating effect exhibited by the above-mentioned compound is unsatisfactory.

Bronchodilators, such as xanthine type medicines and $\beta$-receptor stimulants, are widely used as a clinical, therapeutic agent for treatment of respiratory diseases, such as asthma. It is believed that these medicines increase the concentration of a cyclic adenosine 3',5'-mono-phosphate. As a representative example of the xanthine type medicines, aminophylline can be mentioned. Further, as a representative example of the $\beta$-receptor stimulants, isoproterenol can be mentioned. However, these xanthine type medicines and $\beta$-receptor stimulants have side effects on heart and the like, and an intractable asthma which is not remitted by these medicines has emerged. Therefore, these medicines do not always satisfy the demand of clinicians.

In such a situation, the present inventors have made extensive and intensive studies with a view toward developing a bronchodilator which is more useful for treating respiratory diseases, such as asthma. As a result, it has been found that a sulfonamide derivative which contains an unsubstituted or substituted diazacycloalkyl group or an unsubstituted or substituted aralkylamino group and is substituted with a quinoline residue or an isoquinoline residue, and an acid addition salt thereof have bronchodilatational activity and strongly prevent bronchoconstriction by prostaglandin $F_{2\alpha}$ (hereinafter referred to as "$PGF_{2\alpha}$") which is almost not remitted by the conventional xanthine type bronchodilators. Based on these finding, the present invention has been completed.

Accordingly, it is an object of the present invention to provide a sulfonamide derivative substituted with a quinoline residue or an isoquinoline residue, and an acid addition salt thereof, which not only have excellent bronchodilating activity and no side effect to heart and the like, but also are effective as an active ingredient of medicines for treating an intractable asthma which is not remitted by the xanthine type medicines.

It is another object of the present invention to provide a pharmaceutical composition comprising the above-mentioned derivative or an acid addition salt thereof as an active ingredient, which not only has excellent bronchodilating activity and no side effect to heart, but is also effective for treating an intractable asthma which is not remitted by the xanthine type medicines.

The foregoing and other objects, features and advantages of the present invention will be apparent from the following detailed description and appended claims.

DISCLOSURE OF THE INVENTION

According to the present invention, there is provided a sulfonamide derivative represented by formula (I) or a pharmaceutically acceptable acid addition salt thereof

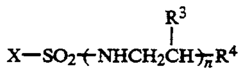

(I)

wherein X represents a quinoline residue represented by formula (II) or an isoquinoline residue represented by formula (III)

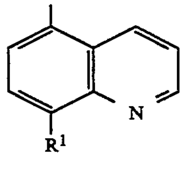

(II)

where $R^1$ is a hydrogen atom, a halogen atom, a lower alkyl group or a lower alkoxy group, or

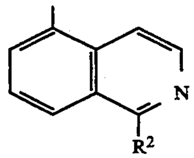

(III)

where $R^2$ is a hydrogen atom or a hydroxyl group, and wherein:

when X is quinoline residue (II), n is zero or 1, in which, when n is zero, $R^4$ is an unsubstituted or substituted diazacycloalkyl group, and when n is 1, $R^3$ is a hydrogen atom or a lower alkyl group and $R^4$ is an unsubstituted or substituted aralkylamino group or an unsubstituted or substituted diazacycloalkyl group; and when X is isoquinoline residue (III), n is 1, in which, $R^3$ is a hydrogen atom or a lower alkyl group and $R^4$ is a 3,4-methylenedioxyphenethylamino group, a 3,4-methylenedioxybenzylamino group or an unsubstituted or substituted diazacycloalkyl group, with the proviso that when $R^4$ is an unsubstituted or substituted diazacycloalkyl group, the diazacycloalkyl group is bonded at a nitrogen atom thereof.

In the above formula (II), $R^1$ is a hydrogen atom, a halogen atom, a lower alkyl group or a lower alkoxy group. Of these, a halogen atom and a lower alkoxy group are most preferred. Examples of halogen atoms include a chlorine atom and a bromine atom. The numbers of carbon atoms of the lower alkyl group and the lower alkoxy group are in the range of from 1 to 6, preferably 1 to 3. Examples of lower alkyl groups include a methyl group and an ethyl group. Examples of lower alkoxy groups include a methoxy group and an ethoxy group.

In the above formula (I), $R^3$ is a hydrogen atom or a lower alkyl group. Of these, a hydrogen atom is most preferred. The number of carbon atoms of the lower alkyl group is in the range of from 1 to 6, preferably 1 to 3. Examples of lower alkyl groups include a methyl group and an ethyl group.

When X is a quinoline residue of formula (II), an unsubstituted or substituted aralkyl moiety of an unsubstituted or substituted aralkyl amino group as $R^4$ is represented by the following formula (IV):

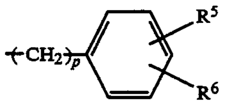

(IV)

wherein p represents an integer of from 1 to 3, each of $R^5$ and $R^6$ independently represents a hydrogen atom, a lower alkyl group, a lower alkoxy group, a halogen atom or a trifluoromethyl group and, $R^5$ and $R^6$ may be directly bonded with each other to form a methylenedioxy group. The number of carbon atoms of each of the lower alkyl group and lower alkoxy group is preferably in the range of from 1 to 3.

Examples of unsubstituted aralkylamino groups include a benzylamino group, a phenethylamino group and the like. Examples of substituted aralkylamino groups include 3,4-dimethoxyphenethylamino group, 4-methoxyphenethylamino group, 3-chlorophenethylamino group, 4-trifluoromethylphenethylamino group, 3,4-methylenedioxyphenethylamino group, 3,4-dimethoxybenzylamino group, 4-methoxybenzylamino group, 3-chlorobenzylamino group, 3,4-methylenedioxybenzylamino group and the like.

When X is quinoline residue (II) or isoquinoline residue (III), the diazacycloalkyl moiety of an unsubstituted or substituted diazacycloalkyl group as $R^4$, has generally 3 to 7 carbon atoms. Examples of unsubstituted diazacycloalkyl groups include a piperazinyl group, homopiperazinyl group and the like. Substituents of the substituted diazacycloalkyl group are the same as the groups represented by the above-mentioned formula (IV).

Examples of substituted diazacycloalkyl groups include 4-(3,4-dimethoxyphenethyl)homopiperazinyl group, 4-(4-methoxylphenethyl)homopiperazinyl group, 4-(3-chlorophenethyl)homopiperazinyl group, 4-(4-trifluoromethylphenethyl)homopiperazinyl group, 4-(3,4-methylenedioxyphenethyl)homopiperazinyl group, 4-(3,4-dimethoxybenzyl)homopiperazinyl group, 4-(4-methoxybenzyl)homopiperazinyl group, 4-(4-chlorobenzyl)homopiperazinyl group, 4-(3,4-methylenedioxybenzyl)homopiperazinyl group, 4-(3,4-dimethoxyphenethyl)piperazinyl group, 4-(4-methoxyphenethyl)piperazinyl group, 4-(3-chlorophenethyl)piperazinyl group, 4-(4-trifluoromethylphenethyl)piperazinyl group, 4-(3,4-methylenedioxyphenethyl)piperazinyl group, 4-(3,4-dimethoxybenzyl)piperazinyl group, 4-(4-methoxybenzyl)piperazinyl group, 4-(3-chlorobenzyl)piperazinyl group, 4-(3,4-methylenedioxybenzyl)piperazinyl group and the like.

In the present invention, $R^4$ is preferably an unsubstituted or substituted diazacycloalkyl group. Further, when X is isoquinoline residue (III), 3,4-methylenedioxyphenethylamino group or 3,4-methylenedioxybenzylamino group may also preferably be used as $R^4$.

Examples of sulfonamide derivatives represented by formula (I) of the present invention include the following compounds.

(1) N-[2-(3,4-methylenedioxyphenethylamino)ethyl]-5-isoquinolinesulfonamide (2) N-[2-(3,4-methylenedioxyphenethylamino)ethyl]-1-hydroxy-5-isoquinolinesulfonamide hydrochloride (3) N-[2(3,4-methylenedioxybenzylamino)ethyl]-5-isoquinolinesulfonamide (4) N-[2-(3,4-methylenedioxybenzylamino)ethyl]-1-hydroxy-5-isoquinolinesulfonamide hydrochloride (5) N-[2-(4-methoxyphenethylamino)ethyl]-8-chloro-5-quinolinesulfonamide (6) N-[2-(4-chlorophenethylamino)ethyl]-8-chloro-5-quinolinesulfonamide (7) N-[2-(4-trifluoromethylphenethylamino)ethyl]-8-chloro-5-quinolinesulfonamide (8) N-[2-(3,4-dimethoxyphenethylamino)ethyl]-8-chloro-5-quinolinesulfonamide (9) N-[2-(3,4-methylenedioxyphenethylamino)ethyl]-8-chloro-5-quinolinesulfonamide

(10) N-[2-(3-chlorobenzylamino)ethyl]-8-chloro-5-quinolinesulfonamide

(11) N-[2-(4-methoxybenzylamino)ethyl]-8-chloro-5-quinolinesulfonamide

(12) N-[2-(3,4-dimethoxybenzylamino)ethyl]-8-chloro-5-quinolinesulfonamide

(13) N-[2-(3,4-methylenedioxybenzylamino)ethyl]-8-chloro-5-quinolinesulfonamide

(14) N-[2-(benzylaminoethyl)-8-chloro-5-quinolinesulfonamide

(15) N-[2-(phenethylaminoethyl)-8-chloro-5-quinolinesulfonamide
(16) N-[2-(4-methoxyphenethylamino)ethyl]-8-ethoxy-5-quinolinesulfonamide
(17) N-[2-(4-chlorophenethylamino)ethyl]-8-ethoxy-5-quinolinesulfonamide
(18) N-[2-(4-trifluoromethylphenethylamino)ethyl]-8-ethoxy-5-quinolinesulfonamide
(19) N-[2-(3,4-dimethoxyphenethylamino)ethyl]-8-ethoxy-5-quinolinesulfonamide
(20) N-[2-(3,4-methylenedioxyphenethylamino)ethyl]-8-ethoxy-5-quinolinesulfonamide
(21) N-[2-(3-chlorobenzylamino)ethyl]-8-ethoxy-5-quinolinesulfonamide
(22) N-[2-(4-methoxybenzylamino)ethyl]-8-ethoxy-5-quinolinesulfonamide
(23) N-[2-(3,4-dimethoxybenzylamino)ethyl]-8-ethoxy-5-quinolinesulfonamide
(24) N-[2-(3,4-methylenedioxybenzylamino)ethyl]-8-ethoxy-5-quinolinesulfonamide
(25) N-(2-benzylaminoethyl)-8-ethoxy-5-quinolinesulfonamide
(26) N-(2-phenethylaminoethyl)-8-ethoxy-5-quinolinesulfonamide
(27) N-[2-(3,4-methylenedioxybenzylamino)ethyl]-5-quinolinesulfonamide
(28) 1-(5-isoquinolinesulfonylaminoethyl)piperazine
(29) 1-(5-isoquinolinesulfonylaminoethyl)homopiperazine
(30) 1-(5-isoquinolinesulfonylaminoethyl)-4-(3,4-methylenedioxybenzyl)piperazine
(31) 1-(5-isoquinolinesulfonylaminoethyl)-4-(3,4-methylenedioxybenzyl)homopiperazine
(32) 1-(1-hydroxy-5-isoquinolinesulfonylaminoethyl) piperazine hydrochloride
(33) 1-(1-hydroxy-5-isoquinolinesulfonylaminoethyl) homopiperazine hydrochloride
(34) 1-(1-hydroxy-5-isoquinolinesulfonylaminoethyl)-4-(3,4-methylenedioxybenzyl)piperazine hydrochloride
(35) 1-(1-hydroxy-5-isoquinolinesulfonylaminoethyl)-3-(3,4-methylenedioxybenzyl)homopiperazine hydrochloride
(36) 1-(8-chloro-5-quinolinesulfonylaminoethyl)-homopiperazine
(37) 1-(8-chloro-5-quinolinesulfonylaminoethyl) piperazine
(38) 1-(8-chloro-5-quinolinesulfonylaminoethyl)-4-(3,4-methylenedioxybenzyl)homopiperazine
(39) 1-(8-chloro-5-quinolinesulfonylaminoethyl)-4-(3,4-methylenedioxybenzyl)piperazine
(40) 1-(8-chloro-5-quinolinesulfonylaminoethyl)-4-(4-chlorobenzyl)homopiperazine
(41) 1-(8-chloro-5-quinolinesulfonylaminoethyl)-4-(4-chlorobenzyl)piperazine
(42) 1-(8-chloro-5-quinolinesulfonylaminoethyl)-4-(3,4-dimethoxyphenethyl)homopiperazine
(43) 1-(8-chloro-5-quinolinesulfonylaminoethyl)-4-(3,4-dimethoxyphenethyl)piperazine
(44) 1-(5-quinolinesulfonylaminoethyl)homopiperazine
(45) 1-(5-quinolinesulfonylaminoethyl)-4-(3,4-methylenedioxybenzyl)homopiperazine
(46) 1-(8-ethoxy-5-quinolinesulfonylaminoethyl) homopiperazine
(47) 1-(8-ethoxy-5-quinolinesulfonylaminoethyl) piperazine
(48) 1-(8-ethoxy-5-quinolinesulfonylaminoethyl)-4-(3,4-methylenedioxybenzyl)homopiperazine
(49) 1-(8-ethoxy-5-quinolinesulfonylaminoethyl)-4-(3,4-methylenedioxybenzyl)piperazine
(50) 1-(8-ethoxy-5-quinolinesulfonylaminoethyl)-4-(4-chlorobenzyl)homopiperazine
(51) 1-(8-ethoxy-5-quinolinesulfonylaminoethyl)-4-(4-chlorobenzyl)piperazine
(52) 1-(8-ethoxy-5-quinolinesulfonylaminoethyl)-4-(3,4-dioxyphenethyl)homopiperazine
(53) 1-(8-ethoxy-5-quinolinesulfonylaminoethyl)-4-(3,4-dimethoxyphenethyl)piperazine
(54) 1-(8-chloro-5-quinolinesulfonyl)homopiperazine
(55) 1-(8-ethoxy-5-quinolinesulfonyl)homopiperazine
(56) 1-(8-chloro-5-quinolinesulfonyl)piperazine
(57) 1-(8-ethoxy-5-quinolinesulfonyl)piperazine
(58) 1-(5-quinolinesulfonyl)homopiperazine
(59) 1-(5-quinolinesulfonyl)piperazine
(60) N-[2-(3,4-dimethoxyphenethylamino)-2-methylethyl]-8-chloro-5-quinolinesulfonamide Further, according to the present invention, there is also provided an acid addition salt of the sulfonamide derivative represented by the above-mentioned formula (I). This salt is a pharmacologically acceptable, non-toxic salt. Examples of salts include salts with inorganic acids, such as hydrochloric acid, hydrobromic acid, phosphoric acid and sulfuric acid, and organic acids, such as acetic acid, citric acid, tartaric acid, lactic acid, succinic acid, fumaric acid, maleic acid and methanesulfonic acid.

The sulfonamide derivative of the present invention can be produced by various methods and is not particularly limited. For example, there can be mentioned a method in which a substituted quinolinesulfonic acid or isoquinolinesulfonic acid which has the above-mentioned substituent $R^1$ or $R^2$ is reacted with thionyl chloride or the like to thereby convert the sulfonic acid group to a sulfonyl chloride group to obtain a sulfonyl chloride compound and then, the obtained sulfonyl chloride compound is reacted with a diazacycloalkane corresponding to substituents $R^4$ mentioned above, to thereby obtain a sulfonamide deviative, or a method in which the sulfonyl chloride compound mentioned above is successively reacted with a hydroxylamine having the above-mentioned substituent $R^3$ and paratoluenesulfonyl chloride and the resultant reaction product is then reacted with a compound corresponding to substituents $R^4$ mentioned above, that is, a diazacycloalkane, an aralkylamine, 3,4-methylenedioxyphenethylamine or 3,4-methylenedioxybenzylamine to thereby obtain a sulfonamide derivative. The acid addition salt of the sulfonamide derivative of the present invention can readily be prepared by reacting the sulfonamide derivative obtained by the method mentioned above with an inorganic acid or an organic acid. When the produced compound per se is an acid addition salt, the corresponding compound in free form can easily be formed by treating with an alkali.

Hereinbelow, representative examples of methods for producing the sulfonamide derivative and acid addition salt thereof of the present invention are described in detail.

(Method 1): Production of the sulfonamide derivative represented by formula (I), wherein X is isoquinoline residue (III), n is 1, $R^2$ is a hydrogen atom, $R^3$ is a hydrogen atom or a lower alkyl group and $R^4$ is a 3,4-methylenedioxyphenethylamino group or a 3,4-methylenedioxybenzylamino group, or wherein X is quinoline residue (II), n is 1, $R^1$ is a hydrogen atom, a halogen atom, a lower alkyl group or a lower alkoxy group, $R^3$ is a hydrogen atom or a lower alkyl group and $R^4$ is an aralkylamino group which is unsubstituted or substituted at its aromatic ring.

5-Isoquinolinesulfonic acid or 8-R'-substituted 5-quinolinesulfonic acid is reacted with thionyl chloride in the presence of a catalytically effective amount (usually 0.5 to 5% by volume based on the amount of thionyl chloride) of N,N-dimethyl-formamide, thereby obtaining 5-isoquinolinesulfonyl chloride or 8-R'-substituted 5-quinolinesulfonyl chloride represented by the following formula (V):

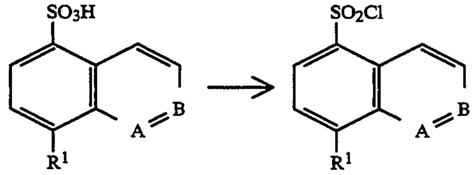
(V)

wherein $R^1$ has the same meaning as defined for formula (II) and A and B each represent a nitrogen atom or carbon atom with the proviso that when A is a nitrogen atom, B is a carbon atom and when A is a carbon atom, B is a nitrogen atom.

The compound of formula (V) is then reacted with the compound represented by the following formula (VI), thereby obtaining a compound represented by the following formula (VII):

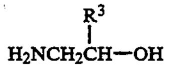
(VI)

wherein $R^3$ has the same meaning as defined in formula (I),

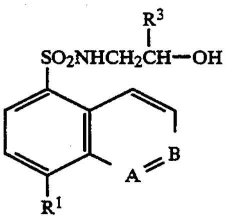
(VII)

wherein $R^1$, $R^3$, A and B have the same meanings as defined above.

Representative examples of compounds represented by formula (VI) which may be employed include ethanolamine, 2-hydroxypropylamine and 2-hydroxybutylamine.

The reaction between the compound of formula (V) and the compound of formula (VI) may be carried out in the presence or absence of an acid acceptor. Examples of acid acceptors which may be employed include alkali metal compounds, such as sodium hydrogencarbonate, sodium hydroxide, potassium carbonate, sodium carbonate, potassium hydroxide and sodium methylate, and organic tertiary amines, such as pyridine, trimethylamine and triethylamine.

The reaction between the compound of formula (V) and the compound of formula (VI) may be carried out in a solvent. Examples of solvents which may be employed include halogenated hydrocarbons, such as dichloromethane and chloroform; ethers such as tetrahydrofuran, dioxane and diethyl ether; dimethyl sulfoxide; N,N-dimethylformamide; acetonitrile; water; and the like. These solvents may be used individually or in mixture.

The amount of the compound of formula (VI) may be in the range of from 1 to 20 mols, preferably from 1 to 10 mols per mol of the compound of formula (V). It is more preferred that the amount of the compound of formula (VI) be in the range of from 2.5 to 5 mols per mol of the compound of formula (V) when an acid acceptor is absent, and in the range of from 1 to 3 mols per mol of the compound of formula (V) when an acid acceptor is present.

When an acid acceptor is employed, the amount of the acid acceptor may be in the range of from 1 to 10 mols, preferably 1 to 6 mols per mol of the compound of formula (VI). The reaction temperature is generally in the range of from −30° to 120° C., preferably −20° to 50° C. The reaction time is generally 0.5 to 48 hours, preferably 0.5 to 6 hours.

The compound of formula (VII) is then reacted with paratoluenesulfonyl chloride to obtain a compound represented by the formula (VIII). This reaction may be conducted according to the method described in L. F. Fieser and M. Fieser, "Reagent for Organic Synthesis", Volume 1, p.1180.

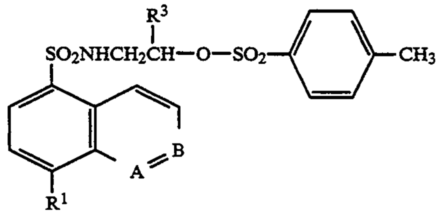
(VIII)

wherein $R^1$ $R^3$ A and B have the same meanings as defined above.

For example, the compound of formula (VII) is dissolved in pyridine, and to the resultant solution is added paratoluenesulfonyl chloride in an amount of 1 to 2 mols per mol of the compound of formula (VII). The reaction is allowed to proceed at 10° to 80° C. for 2 to 8 hours, whereby the compound of formula (VIII) is obtained in high yield.

Next, the compound of formula (VIII) is reacted with 3,4-methylenedioxyphenethylamine or 3,4-methylenedioxybenzylamine when A is a carbon atom and B is a nitrogen atom, or with an aralkylamine which is unsubstituted or substituted at its aromatic ring when A is a nitrogen atom and B is a carbon atom, thereby obtaining the desired compound. Examples of employable aralkylamines having an unsubstituted or substituted aromatic ring, include 3,4-dimethoxyphenethylamine, 4-methoxyphenethylamine, 3-chlorophenethylamine, 4-trifluoromethylphenethylamine, 3,4-methylenedioxyphenethylamine, 3,4-dimethoxybenzylamine, 4-methoxybenzylamine, 3-chlorobenzylamine, 3,4-methylenedioxybenzylamine and the like. These amines are generally used in an amount of from 1 to 10 mols per mol of the compound of formula (VIII). This reaction is preferably conducted in a sealed vessel, since this reaction is likely to proceed slowly. It is preferred that this reaction be carried out in a solvent. Examples of solvents which can be employed include alcohols, such as methanol, ethanol and butanol; halogenated hydrocarbons, such as dichloromethane and chloroform; and ethers, such as tetrahydrofuran, dioxane and diethyl ether; and the like. These solvents may be used individually or in mixture.

The reaction temperature is generally in the range of from 10° to 120° C., preferably 60° to 110° C. The reaction time is generally 0.5 to 72 hours.

(Method 2): Production of the sulfonamide derivative represented by formula (I), wherein X is isoquinoline residue (III), n is 1, $R^2$ is a hydrogen atom, or where in X is quinoline residue (II), n is 1, $R^1$ is a hydrogen atom, a halogen atom, a lower alkyl group or a lower alkoxy group, and wherein, in either case, $R^3$ is a hydrogen atom or a lower alkyl group and $R^4$ is an unsubstituted or substituted diazacycloalkyl group.

The compound of formula (VIII) which has been obtained in the same manner as in Method 1, is reacted with an unsubstituted or substituted diazacycloalkane, thereby obtaining the desired compound.

Representative examples of unsubstituted or substituted diazacycloalkanes which may be used include homopiperazine, piperazine, 1-(3,4-dimethoxyphenethyl) homopiperazine, 1-(4-methoxyphenethyl)-homopiperazine, 1-(3-chlorophenethyl)homopiperazine, 1-(4-trifluoromethylphenethyl)homopiperazine, 1-(3,4-methylenedioxyphenethyl)homopiperazine, 1-(3,4-dimethoxybenzyl) homopiperazine, 1-(4-methoxybenzyl)homopiperazine, 1-(3-chlorobenzyl)homopiperazine, 1-(3,4-methylenedioxybenzyl)homopiperazine, 1-(3,4-dimethoxyphenethyl) piperazine, 1-(4-methoxyphenethyl)piperazine, 1-(3-chlorophenethyl)piperazine, 1-(4-trifluoromethylphenethyl)piperazine, 1-(3,4-methylenedioxyphenethyl) piperazine, 1-(3,4-dimethoxybenzyl)piperazine, 1-(4-methoxybenzyl)piperazine, 1-(3-chlorobenzyl)piperazine, 1-(3,4-methylenedioxybenzyl)piperazine and the like. These amines are generally used in an amount of from 1 to 10 mols per mol of the compound of formula (VIII). This reaction is preferably conducted in a sealed vessel, since this reaction is likely to proceed slowly. It is preferred that this reaction be carried out in a solvent. Examples of solvents which can be employed include alcohols, such as methanol, ethanol and butanol; halogenated hydrocarbons, such as dichloromethane and chloroform; and ethers, such as tetrahydrofuran, dioxane and diethyl ether. These solvents may be used individually or in mixture.

The reaction temperature is generally in the range of from 10° to 120° C., preferably 60° to 110° C. The reaction time is generally 0.5 to 72 hours.

(Method 3): Production of the acid addition salt of the sulfonamide derivative represented by formula (I), wherein X is isoquinoline residue (III), n is 1, $R^2$ is a hydroxyl group, $R^3$ is a hydrogen atom or a lower alkyl group and $R^4$ is a 3,4-methylenedioxyphenethylamino group, 3,4-methylenedioxybenzylamino group, or an unsubstituted or substituted diazacycloalkyl group.

The reaction is conducted in substantially the same manner as in Method 1 and Method 2 except that 1-chloro-5-isoquinoline sulfonic acid is employed instead of 5-isoquinoline sulfonic acid or an 8-R'-substituted 5-quinoline sulfonic acid used in Method 1. The resultant compound is treated with an aqueous solution of an inorganic acid to effect hydrolysis, thereby obtaining the desired compound in which $R^2$ is a hydroxyl group and which is in the form of an acid addition salt.

Examples of inorganic acids include hydrochloric acid, sulfuric acid, hydrobromic acid and the like. The concentration of the inorganic acid is preferably 0.25 to 10 mols/liter.

The reaction temperature is generally in the range of from 50° to 100° C. The reaction time is generally 2 to 6 hours.

(Method 4): Production of the sulfonamide derivative represented by formula (I), wherein X is quinoline residue (II), n is 0, $R^1$ is a hydrogen atom, a halogen atom, a lower alkyl group or a lower alkoxy group, and $R^4$ is an unsubstituted or substituted diazacycloalkyl group.

An 8-R'-substituted 5-quinolinesulfonic acid is reacted with thionyl chloride in the presence of a catalytically effective amount (usually 0.5 to 5% by volume based on the amount of thionyl chloride) of N,N-dimethylformamide in the same manner as in Method 1, thereby obtaining an 8-R'-substituted 5-quinolinesulfonyl chloride. The thus obtained product is reacted with an unsubstituted or substituted diazacycloalkane, to obtain the desired compound.

With respect to examples of unsubstituted or substituted diazacycloalkanes, the same compounds as mentioned in connection with Method 2 can be used.

The reaction between an 8-R'-substituted 5-quinolinesulfonyl chloride and an unsubstituted or substituted diazacycloalkane may be carried out in the presence or absence of an acid acceptor. Examples of acid acceptors which may be employed include alkali metal compounds, such as sodium hydrogencarbonate, sodium hydroxide, potassium carbonate, sodium carbonate, potassium hydroxide and sodium methylate, and organic tertiary amines, such as pyridine, trimethylamine and triethylamine.

The above reaction may be carried out in a solvent. Examples of solvents include halogenated hydrocarbons, such as dichloromethane and chloroform; ethers, such as tetrahydrofuran, dioxane and diethyl ether; dimethyl sulfoxide; N,N-dimethylformamide; acetonitrile; and water. These solvents may be used individually or in mixture.

The amount of diazacycloalkane may be in the range of from 1 to 20 mols, preferably from 1 to 10 mols per mol of 8-R'-substituted 5-quinolinesulfunyl chloride. More preferred amount of diazacycloalkane is in the range of from 2.5 to 5 mols per mol of 8-R'-substituted 5-quinolinesulfonyl chloride when an acid acceptor is absent, and of from 1 to 3 mols per mol of 8-R'-substituted 5-quinolinesulfonyl chloride when an acid acceptor is present.

When an acid acceptor is employed, the amount of the acid acceptor may be in the range of from 1 to 10 mols, preferably 1 to 6 mols per mol of diazacycloalkane. The reaction temperature may generally be in the range of from −30° to 120° C., preferably −20° to −50° C. The reaction time is generally 0.5 to 48 hours, preferably 0.5 to 6 hours.

(Method 5): Production of an acid addition salt from each of the sulfonamide derivatives obtained in Methods 1, 2, and 4.

The compound obtained in Method 1, Method 2 or Method 4 is dissolved in an alcohol, such as methanol and ethanol, to obtain a solution. Then, an equivalent or several fold amount of an acid is added to the solution, to form an acid addition salt. Examples of usable acids include inorganic acids, such as hydrochloric acid, hydrobromic acid, phosphoric acid and sulfuric acid, and organic acids, such as acetic acid, citric acid, tartaric acid, lactic acid, succinic acid, fumaric acid, maleic acid and methanesulfonic acid.

The sulfonamide derivative and the pharmaceutically acceptable acid addition salt thereof of the present invention exert an excellent bronchial smooth muscle relaxation action. Accordingly, these compounds are useful substances for prevention and treatment of respiratory organ diseases, such as asthma.

Accordingly, in a further aspect of the present invention, there is provided a pharmaceutical composition comprising the sulfonamide derivative represented by formula (I) or a pharmaceutically acceptable acid addition salt thereof, and at least one pharmaceutically acceptable carrier or diluent.

Examples of carriers which may be employed include vehicles, such as lactose, sucrose, glucose, starch and crystalline cellulose; binders, such as hydroxypropyl cellulose, carboxymethyl cellulose, starch, gum arabic, gelatin, glucose, sucrose, tragacanth and sodium alginate; disintegrators, such as carboxymethyl cellulose, starch and calcium carbonate; lubricants, such as magnesium stearate, refined tarc, stearic acid and calcium stearate; additives such as lecithine, soybean oil and glycerin; and the like. Examples of diluents include distilled water, physiological saline, Ringer's solution, ethanol, vegetable oil, and mixtures thereof. In the case where the compounds of the present invention are formulated into an inhalant, polychloromonofluoromethane or the like may be used as a solvent.

Further, the compound of the present invention may be used in combination with other drugs, depending on the symptoms of a patient. For example, the compound may be used in combination with other bronchodilators, antiallegic agents, steroids, expectorants and antibiotics.

When the compound of the present invention administered to human, the compound may be orally administered in the form of tablet, powder, granule, capsule, sugar-coated tablet, suspension and syrup, or parenterally administered in the form of solution or suspension for injection, cream and spray. The dose is varied depending on the age, weight, condition, etc. of the patient. However, the dose may generally be 3 to 300 mg per day for an adult. The daily dose may be administered at one time, or it may also be devided into 2 or 3 portions and these portions are administered at intervals. The administration is generally continued for a period of from several days to 2 months. The daily dose and the administration period are varied to some extent depending on the condition of the patient.

The bronchial smooth muscle-relaxing action of the sulfonamide derivative of the present invention was evaluated by the effect on suppression of KCl-induced contraction and $PGF_{2\alpha}$-induced contraction of bronchial specimens excised from guinea pigs. The results are as follows.

The compound of the present invention not only inhibits the contraction induced by the action of KCl which is a bronchial smooth muscle-contracting substance, but also strongly inhibits the contraction induced by the action of PGF2α. For example, the concentrations (hereinafter referred to as "$ED_{50}$") of 1-(8-chloro-5-quinolinesulfonylaminoethyl)-4-(3,4-methylenedioxybenzyl)homopiperazine (38) which are effective for attaining a 50% relaxation of the bronchial smooth muscles contracted by KCl and $PGF_{2\alpha}$, respectively, are 26 μM and 74 μM. The $ED_{50}$ values of N-[2-(3,4-methylenedioxybenzylamino)ethyl]-5-isoquinolinesulfonamide (3) in respect of the inhibitions of KCl-induced contraction and $PGF_{2\alpha}$-induced contraction are 5.2 μM and 23 μM, respectively. By contrast, aminophylline which is a xanthine derivative does not exhibit a 50% relaxation of $PGF_{2\alpha}$-induced contraction even when administered in an amount as large as 200 μM. The $ED_{50}$ values of N-(2-aminoethyl)-N-hexyl-5-isoquinolinesulfonamide hydrochloride [comparative compound (1)] and 1-(5-isoquinolinesulfonyl)-3-aminopiperidine hydrochloride [comparative compound (2)], which are conventional compounds, in respect of the inhibition of $PGF_{2\alpha}$-induced contraction, are 101 μM and 93 μM, respectively.

Further, the inhibiting action of the compound of the present invention on the histamine-induced contraction of the trachea of a guinea pig was examined by in vivo experiment. As a result, the in vivo bronchodilation action was confirmed. That is, in the in vivo experiment on the trachea of a guinea pig, 1-(8-chloro-5-quinolinesulfonylaminoethyl)-4-(3,4-methylenedioxybenzyl)homopiperazine (38) and N-[2-(3,4-methylenedioxybenzylamino)ethyl]-5-isoquinolinesulfonamide (3) respectively suppressed 45% and 36% of the bronchial contraction induced by intravenous administration of 1 mg/kg of histamine. By contrast, aminophylline, comparative compound (1) and comparative compound (2), which were used as controls, respectively suppressed only 7%, 9% and 12% of the bronchial contraction induced by intravenous administration of 1 mg/kg of histamine.

As described above, the sulfonamide derivative of the present invention exhibits an excellent bronchial smooth muscle relaxation action, suggesting that it is a useful substance as a medicine for the prevention and treatment of respiratory organ diseases, such as asthma.

Particularly, in view of the fact that in recent years, a number of publications report that prostaglandins have some part in respiratory diseases, such as asthma [see Lambley, J. E. and Smith, A. P., European Journal of Pharmacology, Vol. 30, pp. 148–153 (1975) and Orehek, J. et al., Journal of Pharmacology & Experimental Therapeutics, Vol. 194, pp. 554–564 (1975)], it is strongly suggested that the compound of the present invention which exhibits strong inhibitory action not only on the KCl or histamine-induced bronchial contraction, but also on the $PGF_{2\beta}$-induced bronchial contraction which is almost not affected by any conventional bronchodilator, has clinical usefulness.

BEST MODE FOR CARRYING OUT THE INVENTION

In each of the following Examples, the yields of the desired compounds of the present invention as shown in Tables 2, 4, 6, 8, 10, 12 and 14 are determined relative to the amount of a sulfonamide which is used in each Example for the reaction between the sulfonamide and an amine for bonding $R^4$ shown in formula (I). On the other hand, the yields of desired compounds of the present invention as shown in Table 16 are determined relative to the amount of 8-ethoxy-5-quinolinesulfonic acid or 5-quinolinesulfonic acid which is used in each Example shown in Table 16.

Hereinbelow, the present invention will be described in detail with reference to the following Examples but they should not be construed to be limiting the scope of the present invention.

EXAMPLE 1

52.8 g of 5-isoquinolinesulfonyl chloride hydrochloride was dissolved in 200 ml of water and extracted with 300 ml of dichloromethane. The resultant aqueous layer was taken out and adjusted to pH 5 with a saturated aqueous sodium hydrogencarbonate solution, and subjected to extraction with 200 ml dichloromethane. Then, the dichloromethane layers were mixed together and added dropwise to a dichloromethane solution (300 ml) containing 24.4 g of ethanolamine over 30 minutes while cooling with ice. The precipitated crystal was subjected to filtration, washed successively with 300 ml of water and 200 ml of ethyl acetate, and dried under reduced pressure at 40° C., to thereby obtain 40.0 g of N-(2-hydroxyethyl)-5-isoquinolinesulfonamide (yield: 79%).

The thus obtained 40.0 g of the N-(2-hydroxyethyl)-5-isoquinolinesulfonamide was dissolved in 103 ml of pyridine. To the resultant solution was added 33.3 g of paratoluenesulfonyl chloride and stirred at room temperature for 24 hours. After completion of the reaction, the pyridine was removed by distillation under reduced pressure to obtain a residue. The thus obtained residue was dissolved in 500 ml of chloroform and extracted with 300 ml of water. The chloroform layer was dried over anhydrous magnesium sulfate. Then, the chloroform was removed by distillation under reduced pressure to obtain a residue as crystals. The thus obtained residual crystals were suspended in acetone and subjected to filtration, followed by vacuum drying, to thereby obtain 46.5 g of N-(2-paratoluenesulfonyloxyethyl)-5-isoquinolinesulfonamide (yield: 72%).

To 4.06 g of the thus obtained N-(2-paratoluenesulfonyloxyethyl)-5-isoquinolinesulfonamide was added 40 ml of tetrahydrofuran containing 4.53 g of 3,4-methylenedioxybenzylamine. The resultant mixture was heated in a sealed vessel at 100° C. for 17 hours and then, the solvent was removed by distillation under reduced pressure to obtain a residue. The thus obtained residue was subjected to purification by means of a column for chromatography packed with 200 g of silica gel (Wacogel C-200, manufactured by Wako Pure Chemical Industries, Ltd., Japan) using, as an eluent, a mixture of methanol and chloroform (0.5% methanol) to obtain 1.84 g of N-[2-(3,4-methylenedioxybenzylamino)ethyl]-5-isoquinolinesulfonamide (3) (yield: 48%).

NMR spectrum (δppm)($CDCl_3$/$CD_3OD$): 2.5–3.5(6H), 5.9(2H), 6.6–6.8(3H), 7.5–7.8(1H), 8.2–8.8(4H), 9.3(1H).

IR spectrum($cm^{-1}$): 2930, 1620, 1510, 1340, 1250, 1160, 1140, 1020.

Mass spectrum (m/e): 385

EXAMPLE 2

Substantially the same procedure as in Example 1 was repeated except that 4.96 g of 3,4-methylenedioxyphenethylamine was used instead of 3,4-methylenedioxybenzylamine, to thereby obtain 1.95 g of N-[2-(3,4-methylenedioxyphenethylamino)ethyl]-5-isoquinolinesulfonamide (1) (yield: 49%)

NMR spectrum (δppm)($CDCl_3$/$CD_3OD$): 2.4–3.1(8H), 5.9(2H), 6.5–6.8(3H), 7.5–7.8(1H), 8.1–8.7(4H), 9.2(1H)

IR spectrum ($cm^{-1}$): 2930, 1615, 1510, 1330, 1250, 1160, 1140, 1010

Mass spectrum (m/e): 399

EXAMPLE 3

To 14.2 g of 8-chloro-5-quinolinesulfonic acid were added 142 ml of thionyl chloride and 1.42 ml of dimethylformamide. The resultant mixture was heated under reflux for 3 hours and the thionyl chloride was removed by distillation under reduced pressure to obtain a residue. The thus obtained residue was dissolved in 100 ml of ice water and adjusted to pH 6 with a saturated aqueous sodium hydrogencarbonate solution, followed by extraction with 100 ml of dichloromethane. The dichloromethane layer was added dropwise to 100 ml of a dichloromethane solution containing 3.56 g of ethanolamine and 5.6 g of triethylamine over 30 minutes while cooling with ice. The mixture was stirred at a temperature of 15° C. to 20° C. for 2 hours. After completion of the reaction, the resultant mixture was washed with 200 ml of water and dried over anhydrous magnesium sulfate. Then, the solvent was removed by distillation under reduced pressure, to thereby obtain 14.0 g of N-(2-hydroxyethyl)-8-chloro-5-quinolinesulfonamide (yield: 84%).

To 5.74 g of N-(2-hydroxyethyl)-8-chloroquinolinesulfonamide was added 80 ml of pyridine. Then, to the mixture was added 7.6 g of paratoluenesulfonyl chloride and stirred at a temperature of 15° C. to 20° C. for 24 hours. After completion of the reaction, the resultant mixture was put into 200 g of ice water and extracted twice with 200 ml of dichloromethane, followed by drying over anhydrous magnesium sulfate. Then, the solvent was removed by distillation under reduced pressure to obtain a residue. The thus obtained residue was subjected to purification by means of a column for chromatography packed with 250 g of silica gel (Wacogel C-200, manufactured by Wako Pure Chemical Industries, Ltd., Japan) using chloroform as an eluent, to thereby obtain 6.25 g of N-(2-paratoluenesulfonyloxyethyl)-8-chloro-5-quinolinesulfonamide (yield: 71%).

3.32 g of N-(2-paratoluenesulfonyloxyethyl)-8-chloro-5-quinolinesulfonamide was reacted with 30 ml of a tetrahydrofuran solution containing 3.41 g of 3,4-methylenedioxybenzylamine in a sealed vessel at 70° C. for 17 hours, and the solvent was removed by distillation under reduced pressure to obtain a residue. The thus obtained residue was subjected to purification by means of a column for chromatography packed with 200 g of silica gel (Wacogel C-200, manufactured by Wako Pure Chemical Industries, Ltd., Japan) using, as an eluent, a mixture of methanol and chloroform (5% methanol) to thereby obtain 1.80 g of N-[2-(3,4-methylenedioxybenzylamino)ethyl]-8-chloro-5-quinolinesulfonamide (13) (yield: 57%)

NMR spectrum (δppm)($CDDl_3$/$CD_3OD$): 2.5–3.5(6H), 5.9(2H), 6.6–6.8(3H) 7.2–8.2(3H), 8.9–9.1(2H).

IR spectrum ($cm^{-1}$): 2930, 1490, 1330, 1260, 1150, 1135, 1020, 910.

Mass spectrum (m/e): 419

EXAMPLE 4

Substantially the same procedure as in Example 3 was repeated except that 3.41 g of 4-methoxyphenethylamine was used instead of 3,4-methylenedioxybenzylamine, to thereby obtain 2.05 g of N-[2-(4-methoxyphenethylamino)ethyl]-8-chloro-5-quinolinesulfonamide (5) (yield: 65%).

NMR spectrum (δppm)($CDCl_3$/$CD_3OD$):

2.3–3.2(6H), 3.7(2H), 6.6–7.1(3H) 7.3–8.2(3H), 8.0–9.2(2H).

IR spectrum ($cm^{-1}$): 2930, 1485, 1330, 1260, 1150, 1140, 910.

Mass spectrum (m/e): 419

EXAMPLES 5 TO 13

Substantially the same procedure as in Example 3 was repeated except that 4-chlorophenethylamine, 4-trifluorophenethylamine, 3,4-dimethoxyphenethylamine, 3,4-methylenedioxyphenethylamine, 3-chlorobenzylamine, 4-methoxybenzylamine, 3,4-dimethoxybenzylamine, benzylamine and pheneythylamine were individually used in place of 3,4-methylenedioxybenzylamine, to thereby obtain compounds (6), (7), (8), (9), (10), (11), (12), (14) and (15).

The reaction conditions are shown in Table 1. The yields and analytical data of these compounds are shown in Table 2.

TABLE 1

| | Amines used | | Reaction | |
|---|---|---|---|---|
| | Type | Amount (g) | temperature (°C.) | hour |
| Example 5 | 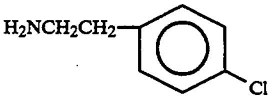 | 3.52 | 90–100 | 10 |
| Example 6 | 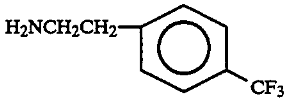 | 4.28 | 90–100 | 10 |
| Example 7 | 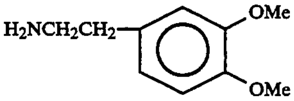 | 4.26 | 90–100 | 14 |
| Example 8 | 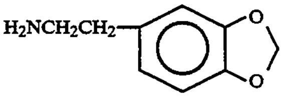 | 3.74 | 90–100 | 14 |
| Example 9 | 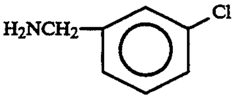 | 3.19 | 90–100 | 24 |
| Example 10 | 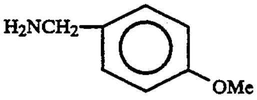 | 3.36 | 90–100 | 24 |
| Example 11 | 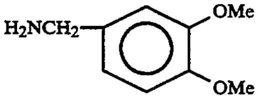 | 3.77 | 90–100 | 17 |
| Example 12 | 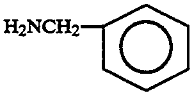 | 2.42 | 90–100 | 14 |
| Example 13 | 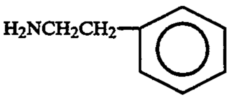 | 2.74 | 90–100 | 14 |

TABLE 2

| | Compound No. | Yield (%) | Mass spectrum (m/e) | NMR spectrum (δ ppm) ($CDCl_3/CD_3OD$) |
|---|---|---|---|---|
| Example 5 | (6) | 72 | 424 | 2.3–3.2(8H), 6.8–7.1(4H) 7.4–8.2(3H), 8.9–9.2(2H) |
| Example 6 | (7) | 75 | 457 | 2.3–3.1(8H), 6.6–7.1(4H), 7.5–8.2(3H), 8.9–9.2(2H) |
| Example 7 | (8) | 66 | 449 | 2.5–3.2(8H), 3.8(6H), 6.4–6.8(3H), 7.4–8.2(3H), 8.9–9.2(2H) |
| Example 8 | (9) | 75 | 433 | 2.4–3.1(8H), 5.9(2H), 6.5–6.8(3H), 7.4–8.1(3H), 8.9–9.2(2H) |
| Example 9 | (10) | 45 | 410 | 2.5–3.5(6H), 6.5–6.8(3H), 6.9–7.3(1H), 7.5–8.1(3H), 8.9–9.2(2H) |
| Example 10 | (11) | 50 | 405 | 2.5–3.5(6H), 3.7(3H), 6.4–6.7(4H), 7.4–8.2(3H), 8.9–9.3(2H) |
| Example 11 | (12) | 52 | 435 | 2.4–3.5(6H), 3.8(6H), 6.4–6.8(3H), 7.4–8.2(3H) |

TABLE 2-continued

| | Compound No. | Yield (%) | Mass spectrum (m/e) | NMR spectrum (δ ppm) ($CDCl_3/CD_3OD$) |
|---|---|---|---|---|
| | | | | 8.9–9.2(2H) |
| Example 12 | (14) | 63 | 375 | 2.5–3.5(6H), 6.4–7.0(5H), 7.4–8.2(3H), 8.9–9.2(2H) |
| Example 13 | (15) | 67 | 389 | 2.4–3.2(8H), 6.4–7.0(5H) 7.4–8.2(3H), 8.9–9.2(2H) |

EXAMPLES 14 TO 24

Substantially the same procedure as described in Examples 3 to 13 was repeated except that 8-ethoxy-5-quinolinesulfonic acid was used instead of 8-chloro-5-quinolinesulfonic acid in order to obtain N-[2-(paratoluenesulfonyloxy)ethyl]-8-ethoxy-5-quinolinesulfonamide and 3.39 g of the thus obtained sulfonamide was used, to thereby obtain compounds (16) to (26), respectively.

The reaction conditions are shown in Table 3 and the yields and analytical data of these compounds are shown in Table 4.

TABLE 3

| | Amines used | | Reaction | |
|---|---|---|---|---|
| | Type | Amount (g) | temperature (°C.) | hour |
| Example 14 | 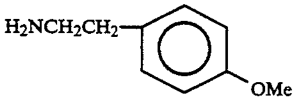 | 3.41 | 90–100 | 14 |
| Example 15 | 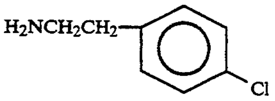 | 3.52 | 90–100 | 14 |
| Example 16 | 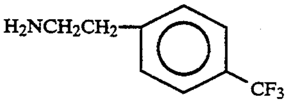 | 4.28 | 90–100 | 14 |
| Example 17 | 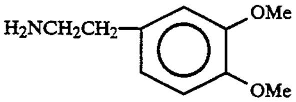 | 4.26 | 90–100 | 14 |
| Example 18 | 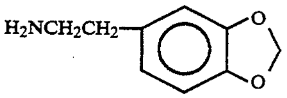 | 3.74 | 90–100 | 24 |
| Example 19 | 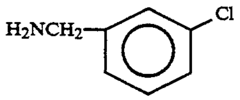 | 3.19 | 90–100 | 24 |
| Example 20 | 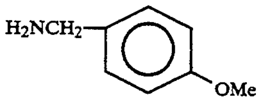 | 3.36 | 90–100 | 17 |
| Example 21 | 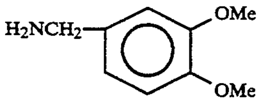 | 3.77 | 90–100 | 14 |
| Example 22 | 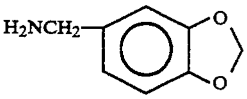 | 3.41 | 90–100 | 14 |
| Example 23 | 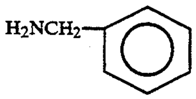 | 2.42 | 90–100 | 14 |

TABLE 3-continued

| | Amines used | | Reaction | |
|---|---|---|---|---|
| | Type | Amount (g) | temperature (°C.) | hour |
| Example 24 | 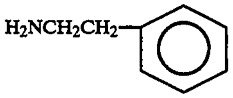 | 2.74 | 90–100 | 14 |

TABLE 4

| | Compound No. | Yield (%) | Mass spectrum (m/e) | NMR spectrum (δ ppm) ($CDCl_3/CD_3OD$) |
|---|---|---|---|---|
| Example 14 | (16) | 65 | 429 | 1.5–2.0(3H), 2.3–3.2(8H) 3.7(3H), 4.1–4.6(2H), 6.8–8.2(7H), 8.9–9.2(2H) |
| Example 15 | (17) | 69 | 433 | 1.5–2.0(3H), 2.3–3.1(8H), 4.1–4.6(2H), 6.6–8.2(7H), 8.9–9.2(2H) |
| Example 16 | (18) | 59 | 467 | 1.5–2.0(3H), 2.5–3.2(8H), 4.1–4.6(2H), 6.6–8.2(7H), 8.9–9.2(2H) |
| Example 17 | (1) | 71 | 459 | 1.5–2.0(3H), 2.5–3.2(8H), 3.8(6H), 4.1–4.6(2H), 6.4–8.1(6H), 8.9–9.2(2H) |
| Example 18 | (20) | 63 | 443 | 1.5–2.0(3H), 2.5–3.3(8H), 4.1–4.6(2H), 5.9(2H), 6.5–8.1(6H), 8.9–.2(2H) |
| Example 19 | (21) | 59 | 419 | 1.5–2.0(3H), 2.5–3.5(6H), 4.1–4.6(2H), 6.5–8.2(7H), 8.9–9.3(2H) |
| Example 20 | (22) | 48 | 415 | 1.5–2.0(3H), 2.5–3.5(6H), 3.7(3H), 4.1–4.6(2H), 6.4–8.2(7H), 8.9–9.2(2H) |
| Example 21 | (23) | 51 | 445 | 1.5–2.0(3H), 2.4–3.5(6H), 3.8(6H), 4.1–4.6(2H), 6.4–8.2(6H), 8.9–9.2(2H) |
| Example 22 | (24) | 55 | 429 | 1.5–2.0(3H), 2.5–3.5(6H), 4.1–4.6(2H), 5.9(2H), 6.6–8.2(6H), 8.9–9.2(2H) |
| Example 23 | (25) | 63 | 385 | 1.5–2.0(3H), 2.5–3.5(6H), 4.1–4.6(2H), 6.4–8.2(8H), 8.9–9.2(2H) |
| Example 24 | (26) | 65 | 399 | 1.5–2.0(3H), 2.5–3.3(8H), 4.1–4.6(2H), 6.4–8.2(8H), 8.9–9.2(2H) |

EXAMPLE 25

Compound (27) was obtained in substantially the same manner as described in Example 3 except that 5-quinolinesulfonic acid was used in place of 8-chloro-5-quinolinesulfonic acid (yield: 52%).

NMR Spectrum (δppm) ($CDCl_3/CD_3OD$): 2.5–3.5(6H), 5.9(2H), 6.6–6.8(3H) 7.4–8.0(2H) 8.2–8.6(2H) 8.8–9.2(2H)

IR absorption spectrum ($cm^{-1}$): 2940, 1490, 1340, 1260, 1150, 1135

Mass spectrum (m/e):385

EXAMPLES 26 TO 29

Compounds (28), (29), (30) and (31) were obtained in substantially the same manner as described in Example 1, except that piperazine, homopiperazine, 1-(3,4-methylenedioxybenzyl)piperazine and 1-(3,4-methylenedioxybenzyl)homopiperazine were individually used in place of 3,4-methylenedioxybenzylamine.

The reaction conditions are shown in Table 5 and the yields and analytical data are shown in Table 6.

TABLE 5

| | Amines used | | Reaction | |
|---|---|---|---|---|
| | Type | Amount (g) | temperature (°C.) | hour |
| Example 26 | 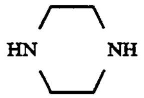 | 2.58 | 90–100 | 17 |
| Example 27 | 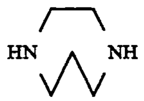 | 3.00 | 90–100 | 17 |
| Example 28 | 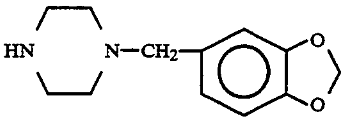 | 6.59 | 90–100 | 14 |
| Example 29 | 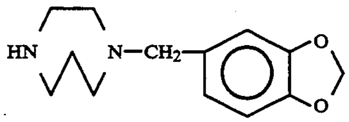 | 7.01 | 90–100 | 14 |

TABLE 6

| | Compound No. | Yield (%) | Mass spectrum (m/e) | NMR spectrum (δ ppm) ($CDCl_3/CD_3OD$) |
|---|---|---|---|---|
| Example 26 | (28) | 42 | 320 | 2.4–3.5(12H), 7.5–7.8 (1H), 8.2–8.8(4H), 9.3(1H) |
| Example 27 | (29) | 48 | 334 | 1.3–1.9(2H), 2.4–3.5 (12H), 7.5–7.8(1H), 8.2–8.8(4H), 9.8(1H) |
| Example 28 | (30) | 63 | 454 | 2.3–3.6(14H), 5.9(2H) 6.7–6.9(3H), 7.5–7.8 |

TABLE 6-continued

| Compound No. | Yield (%) | Mass spectrum (m/e) | NMR spectrum (δ ppm) ($CDCl_3$/$CD_3OD$) |
|---|---|---|---|
| | | | (1H), 8.2–8.8(4H), 9.2(1H) |
| Example 29 | (31) | 66 | 468 | 1.4–1.9(2H), 2.3–3.6 (14H), 5.9(2H), 6.7–6.9(3H), 7.5–7.8(1H), 8.2–8.8(4H), 9.2(1H) |

EXAMPLES 30 TO 37

Compounds (36), (37), (38), (39), (40), (41), (42) and (43) were obtained in substantially the same manner as described in Example 3 except that homopiperazine, piperazine, 1-(3,4-methylenedioxybenzyl)homopiperazine, 1-(3,4-methylenedioxybenzyl)piperazine, 1-(4-chlorobenzyl)homopiperazine, 1-(4-chlorobenzyl)piperazine, 1-(3,4-dimethoxyphenethyl)homopiperazine and 1-(3,4-dimethoxyphenethyl)piperazine were individually used in place of 3,4-methylenedioxybenzylamine.

The reaction conditions are shown in Table 7 and the yields and analytical data are shown in Table 8.

TABLE 7

| | Amines used | | Reaction | |
|---|---|---|---|---|
| | Type | Amount (g) | temperature (°C.) | hour |
| Example 30 | 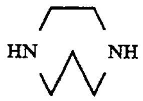 | 2.26 | 90–100 | 17 |
| Example 31 | 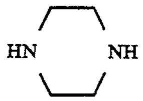 | 1.95 | 90–100 | 17 |
| Example 32 | 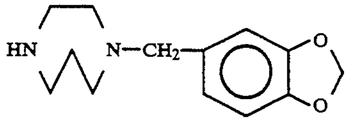 | 5.29 | 90–100 | 17 |
| Example 33 | 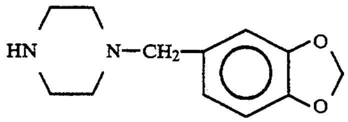 | 4.97 | 90–100 | 17 |
| Example 34 | 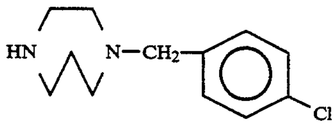 | 5.08 | 90–100 | 17 |
| Example 35 | 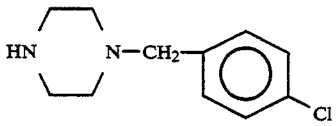 | 4.76 | 90–100 | 17 |
| Example 36 | 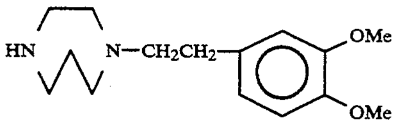 | 5.97 | 90–100 | 17 |
| Example 37 | 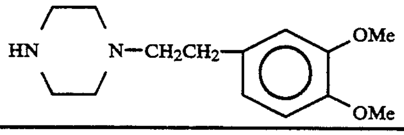 | 5.65 | 90–100 | 17 |

TABLE 8

| | Compound No. | Yield (%) | Mass spectrum (m/e) | NMR spectrum (δ ppm) ($CDCl_3$/$CD_3OD$) |
|---|---|---|---|---|
| Example 30 | (36) | 41 | 368 | 1.4–1.9(2H), 2.3–3.5 (12H), 7.5–8.2(3H), 8.9–9.2(2H) |
| Example 31 | (37) | 43 | 354 | 2.5–3.3(12H), 7.5–8.2 (3H), 8.9–9.2(2H) |
| Example 32 | (38) | 62 | 502 | 1.3–1.9(2H), 2.3–3.5 (14H), 5.9(2H), 6.7–6.9 (3H), 7.5–8.3(3H), 9.0–9.2(2H) |
| Example 33 | (39) | 58 | 488 | 2.3–3.6(14H), 5.9(2H), 6.7–6.9(3H), 7.5–8.3 (3H), 9.0–9.2(2H) |
| Example | (40) | 65 | 493 | 1.3–1.9(2H), 2.3–3.5 |

TABLE 8-continued

| | Compound No. | Yield (%) | Mass spectrum (m/e) | NMR spectrum (δ ppm) ($CDCl_3/CD_3OD$) |
|---|---|---|---|---|
| 34 | | | | (14H), 6.8-7.2(4H), 7.5-8.3(3H), 9.0-9.2 (2H) |
| Example 35 | (41) | 66 | 479 | 2.3-3.6(14H), 6.8-7.2(4H), 7.5-8.3 (3H), 9.0-9.2(2H) |
| Example 36 | (42) | 52 | 532 | 1.3-1.9(2H), 2.3-3.3 (16H), 3.7(6H), 6.4-6.8(3H), 7.5-8.3 (3H), 9.0-9.2(2H) |
| Example 37 | (43) | 58 | 518 | 2.3-3.3(16H), 3.7(6H), 6.4-6.8(3H) 7.5-8.3(3H), 9.0-9.2 (2H) |

EXAMPLES 38 TO 45

Compound (46), (47), (48), (49), (50), (51), (52) and (53) were obtained in substantially the same manner as described in Example 3 except that 8-ethoxy-5-quinolinesulfonic acid was used in place of 8-chloro-5-quinolinesulfonic acid and that homopiperazine, piperazine, 1-(3,4-methylenedioxybenzyl)homopiperazine, 1-(3,4-methylenedioxybenzyl)piperazine, 1-(4-chlorobenzyl)-homopiperazine, 1-(4-chlorobenzyl)piperazine, 1-(3,4-dimethoxyphenethyl)homopiperazine and 1-(3,4-dimethoxyphenethyl)piperazine were individually used in place of 3,4-methylenedioxybenzylamine.

The reaction conditions are shown in Table 9 and the yields and analytical data are shown in Table 10.

TABLE 9

| | Amines used | | Reaction | |
|---|---|---|---|---|
| | Type | Amount (g) | temperature (°C.) | hour |
| Example 38 | 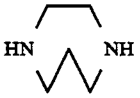 | 2.26 | 90-100 | 17 |
| Example 39 | 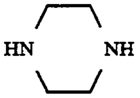 | 1.95 | 90-100 | 17 |
| Example 40 | 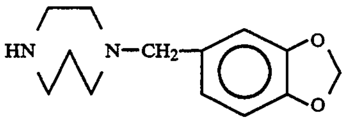 | 5.29 | 90-100 | 17 |
| Example 41 | 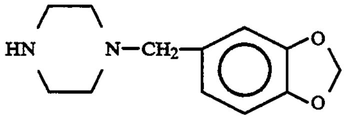 | 4.97 | 90-100 | 17 |
| Example 42 | 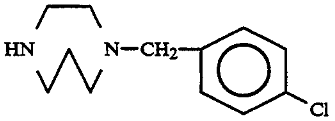 | 5.08 | 90-100 | 17 |
| Example 43 | 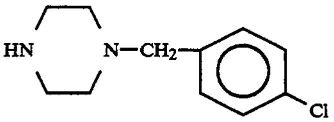 | 4.76 | 90-100 | 17 |
| Example 44 | 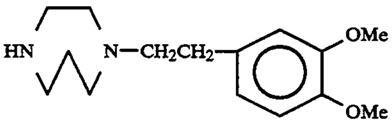 | 5.97 | 90-100 | 17 |
| Example 45 | 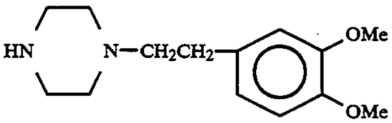 | 5.65 | 90-100 | 17 |

TABLE 10

| | Compound No. | Yield (%) | Mass spectrum (m/e) | NMR spectrum (δ ppm) ($CDCl_3/CD_3OD$) |
|---|---|---|---|---|
| Example 38 | (46) | 42 | 378 | 1.4–2.0(5H), 2.4–3.6 (12H), 4.0–4.6(2H), 6.9–8.2(3H), 8.9–9.2 (2H) |
| Example 39 | (47) | 41 | 364 | 1.5–2.0(3H), 2.5–.5 (12H), 4.0–4.6(2H), 6.9–8.2(3H), 8.9–9.2 (2H) |
| Example 40 | (48) | 66 | 512 | 1.3–1.9(5H), 2.3–3.5 (14H), 4.0–4.6(2H), 5.9(2H), 6.7–6.9(3H), 7.0–8.3(3H), 9.0–9.2 (2H) |
| Example 41 | (49) | 55 | 498 | 1.5–2.0(3H), 2.3–3.6 (14H), 4.0–4.6(2H), 5.9(2H), 6.7–6.9(3H), 7.0–8.3(3H), 9.0–9.2 (2H) |
| Example 42 | (50) | 62 | 502 | 1.3–2.0(5H), 2.3–3.5 (14H), 4.0–4.6(2H), 6.8–8.3(7H), 9.0–9.2 (2H) |
| Example 43 | (51) | 63 | 488 | 1.5–2.0(3H), 2.3–3.6 (14H), 4.0–4.6(2H), 6.8–8.3(7H), 9.0–9.2 (2H) |
| Example 44 | (52) | 56 | 542 | 1.3–1.9(5H), 2.3–3.5 (16H), 3.7(6H), 4.0–4.6(2H), 6.4–6.8 (3H), 7.0–8.3(3H), 9.0–9.2(2H) |
| Example 45 | (53) | 51 | 528 | 1.5–2.0(3H), 2.3–3.5 (16H), 3.7(6H), 4.0–4.6(2H), 6.4–6.8 (3H), 7.0–8.3(3H), 9.0–9.2(2H) |

EXAMPLES 46 TO 47

Compounds (44) and (45) were obtained in substantially the same manner as described in Example 3 except that 5-quinolinesulfonic acid was used in place of 8-chloro-5-quinolinesulfonic acid; that homopiperazine and 1-(3,4-methylenedioxybenzyl)homopiperazine were individually used in place of 3,4-methylenedioxybenzylamine; and that the amount of N-(2-paratoluenesulfonyloxyethyl)-5-quinolinesulfonamide was changed to 3.6 g.

The reaction conditions are shown in Table 11, and the yields and analytical data are shown in Table 12.

TABLE 12

| | Compound No. | Yield (%) | Mass spectrum (m/e) | NMR spectrum (δ ppm) ($CDCl_3/CD_3OD$) |
|---|---|---|---|---|
| Example 46 | (44) | 61 | 334 | 1.4–1.9(2H), 2.4–3.6 (12H), 7.4–8.0(2H), 8.2–8.6(2H), 8.8–9.2 (2H) |
| Example 47 | (45) | 56 | 468 | 1.4–2.0(2H), 2.4–3.6 (14H), 5.9(2H), 6.6–6.9(3H), 7.4–8.0 (2H), 8.2–8.6(2H), 8.8–9.2(2H) |

EXAMPLE 48

8.0 g of 1-chloro-5-isoquinolinesulfonylchloride hydrochloride was dissolved in 40 ml of iced water and the pH of the solution was adjusted to 6 with a saturated aqueous sodium hydrogencarbonate solution, followed by extraction with 67 ml of dichloromethane. The resultant dichloromethane layer was added dropwise into 67 ml of a dichloromethane solution containing 1.69 g of ethanolamine and 2.7 g of triethylamine for 20 minutes and then the mixture was stirred for two hours at 15° to 20 ° C. while cooling with ice.

After completion of the reaction, the mixture was washed with 100 ml of distilled water and was dried over anhydrous magnesium sulfate. Then, the dichloromethane was removed under reduced pressure to obtain 5.74 g of N-(2-hydroxyethyl)-1-chloro-5-isoquinolinesulfonamide (yield: 74%).

To 5.74 g of N-(2-hydroxyethyl)-1-chloro-5-isoquinolinesulfonamide was successively added 80 ml of pyridine and 7.62 g of p-toluenesulfonylchloride and the mixture was stirred at 15° to 20 ° C. for 24 hours. After completion of the reaction, the mixture was cooled with 200 g of ice water and the mixture was subjected to extraction with 200 ml of dichloromethane twice. The resultant dichloromethane layer was dried over anhydrous magnesium sulfate and the residue was subjected to purification by means of a chromatography column packed with 200 g of silica gel (Wacogel C-200, manufactured by Wako Pure Chemical Industries, Ltd., Japan) using chloroform as an eluent to obtain 6.61 g of N-(2-paratoluenesulfonyloxyethyl)-1-chloro-5-isoquinolinesulfonamide (yield: 75%).

30 ml of a tetrahydrofuran solution containing 3.3 g of N-(2-paratoluenesulfonyloxyethyl)-1-chloroisoquinoline and 1.13 g of 3,4-methylenedioxybenzylamine was kept in a sealed vessel at 70 ° C. for 8 hours to advance a reaction.

TABLE 11

| | Amines used Type | Amount (g) | Reaction temperature (°C.) | hour |
|---|---|---|---|---|
| Example 46 | 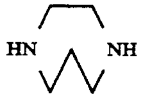 | 2.04 | 90–100 | 14 |
| Example 47 | 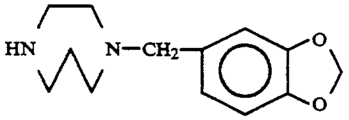 | 4.77 | 90–100 | 14 |

The solvent was removed under reduced pressure and the residue was subjected to purification by means of a chromatography column packed with 200 g of silica gel (Wacogel C-200, manufactured by Wako Pure Chemical Industries, Ltd., Japan) using, as an eluent, a mixture of methanol and chloroform (5% methanol) to thereby obtain 1.57 g of N-[2-(3,4-methylenedioxybenzylamino) ethyl]-1-chloro-5-isoquinolinesulfonamide (yield: 50%).

20 ml of 6(mol/liter) hydrochloric acid was added to 1.50 g of N-[2-(3,4-methylenedioxybenzylamino) ethyl]-1-chloro-5-isoquinolinesulfonamide, and the mixture was heated at 65 ° C. for 6 hours. The resultant crystalline precipitate was filtered off, and washed with 10 ml of ice water twice and then washed with 10 ml of ethanol twice, followed by drying, to thereby obtain 1.3 g of N-[2-(3,4-methylenedioxybenzylamino)ethyl]-1-hydroxy-5-isoquinolinesulfonamide hydrochloride (4) (yield: 83%).

NMR spectrum (δppm) (DMSO-d6): 3.1–3.8(6H), 6.0(2H), 6.7–6.9(3H), 7.0–7.7(3H), 8.2–8.6(2H)

IR spectrum ($cm^{-1}$) 2940, 1685, 1630, 1540, 1350, 1260, 1150, 1130, 1070

Mass spectrum (m/e): 437

EXAMPLES 49 TO 53

Compounds (2), (32), (33), (34) and (35) were obtained in substantially the same manner as described in Example 48 except that 3,4-methylenedioxyphenethylamine, piperzine, homopiperazine, 1-(3,4-methylenedioxybenzyl)piperazine, and 1-(3,4-methylenedioxybenzyl)-homopiperazne were individually used in place of 3,4-methylenedioxybenzylamine.

The reaction conditions are shown in Table 13, and the yields and analytical data are shown in Table 14.

TABLE 13

| | Amines used | | Reaction | |
|---|---|---|---|---|
| | Type | Amount (g) | temperature (°C.) | hour |
| Example 49 | 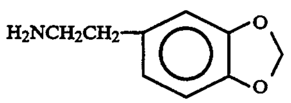 | 1.24 | 60–70 | 10 |
| Example 50 | 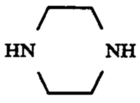 | 0.64 | 60–70 | 10 |
| Example 51 | 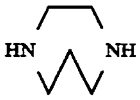 | 0.75 | 60–70 | 10 |
| Example 52 | 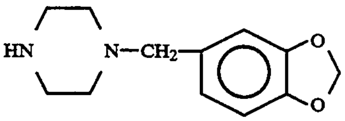 | 1.65 | 60–70 | 10 |
| Example 53 | 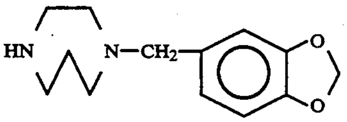 | 1.75 | 60–70 | 10 |

TABLE 14

| | Compound No. | Yield (%) | Mass spectrum (m/e) | NMR spectrum (δ ppm) ($DMSO-d_6$) |
|---|---|---|---|---|
| Example 49 | (2) | 34 | 451 | 2.9–3.8(8H), 6.0(2H), 6.7–6.9(3H), 7.0–7.7 (3H), 8.2–8.6(2H) |
| Example 50 | (32) | 28 | 372 | 2.6–3.8(12H), 7.0–7.7(3H), 8.2–8.6 (2H) |
| Example 51 | (33) | 36 | 386 | 1.4–2.0(2H), 2.6–3.8 (12H), 7.0–7.7(3H), 8.2–8.6(2H) |
| Example 52 | (34) | 31 | 506 | 2.6–3.8(14H), 5.9(2H), 6.7–6.9(3H), 7.0–7.7 (3H), 8.2–8.6(2H) |
| Example 53 | (35) | 29 | 520 | 1.4–2.0(2H), 2.6–3.8 (14H), 5.9(2H), 6.7–6.9(3H), 7.0–7.7 (3H), 8.2–8.6(2H) |

EXAMPLE 54

To 14.2 g of 8-chloro-5-quinolinesulfonic acid were added 142 ml of thionyl chloride and 1.42 ml of dimethylformamide, followed by heating under reflux for 3 hours. Then, the thionyl chloride was removed under reduced pressure and the resultant residue was dissolved in 100 ml of ice water. The pH of the resultant solution was adjusted at 6 with a saturated aqueous sodium hydrogencarbonate solution. The solution was subjected to extraction with 100 ml of dichloromethane. The resultant dichloromethane layer was added dropwise to 100 ml of a dichloromethane solution containing 5.81 g of homopiperazine and 5.6 g of triethylamine over a period of 30 minutes while cooling with ice. The mixture was stirred at a temperature of 15° C. to 20° C. for 2 hours, washed with a 200 ml of water, and dried over anhydrous magnesium sulfate. Then, the solvent was removed under reduced pressure to obtain a residue. The thus obtained residue was subjected to purification by means of a chromatography column packed with 500 g of silica gel (Wacogel C-200, manufactured by Wako Pure Chemicals Industries, Ltd., Japan) and using, as a solvent, a mixture of methanol and chloroform (5% methanol), to thereby obtain 10.2 g of 1-(8-chloro-5-quinolinesulfonyl)homopiperazine (54) (yield: 54%).

NMR spectrum (δppm) ($CDCl_3$/$CD_3OD$): 1.6–2.0(2H), 2.8–3.8(8H), 7.0–8.2(3H), 8.9–9.1(2H).

IR spectrum ($cm^{-1}$): 2930, 1490, 1330, 1260, 1150, 1135, 1020, 910.

Mass spectrum (m/e): 325

EXAMPLE 55

Substantially the same procedure as described in Example 54 was repeated except that 5.0 g of piperazine was used instead of homopiperazine, to thereby obtain 9.6 g of compound (56) (yield: 53%).

NMR spectrum (δppm) ($CDCl_3$/$CD_3OD$): 3.6–4.6(8H), 7.0–8.2(3H), 8.9–9.1(2H).

IR spectrum ($cm^{-1}$): 2930, 1490, 1330, 1260, 1150, 1135, 1020, 910.

Mass spectrum (m/e): 311

EXAMPLES 56 TO 59

In Examples 56 and 57, substantially the same procedure as described in Example 54 was repeated except that 14.8 g of 8-ethoxy-5-quinolinesulfonic acid was used instead of 8-chloro-5-quinolinesulfonic acid, to thereby obtain compounds (55) and (57). In Examples 58 and 59, substantially the same procedure as described in Example 54 was repeated except that 12.2 g of 5-quinolinesulfonic acid was used instead of 8-chloroquinolinesulfonic acid, to thereby obtain compounds (58) and (59).

The reaction conditions are shown in Table 15, and the yields and analytical data of these compounds are shown in Table 16.

TABLE 15

| | Amine used | | Reaction | |
|---|---|---|---|---|
| | Type | Amount (g) | temperature (°C.) | hour |
| Example 56 | 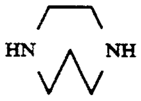 | 5.81 | 15–20 | 2 |
| Example 57 | 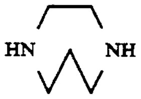 | 5.00 | 15–20 | 2 |
| Example 58 | 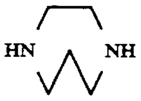 | 5.81 | 15–20 | 2 |
| Example 59 | 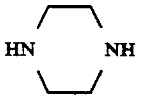 | 5.00 | 15–20 | 2 |

TABLE 16

| | Compound No. | Yield (%) | Mass spectrum (m/e) | NMR spectrum (δ ppm) ($CDCl_3$/$CD_3OD$) |
|---|---|---|---|---|
| Example 56 | (55) | 65 | 335 | 1.6–2.1(5H),<br>2.9–3.7(8H)<br>4.2–4.6(2H),<br>6.9–7.2(3H)<br>8.9–9.2(2H) |
| Example 57 | (57) | 68 | 321 | 1.6–2.1(5H),<br>2.8–3.6(8H)<br>4.2–4.6(2H)<br>6.9–7.2(3H)<br>8.9–9.2(2H) |
| Example 58 | (58) | 59 | 291 | 1.5–2.0(2H),<br>2.8–3.6(8H)<br>7.4–8.0(2H),<br>8.2–8.6(2H)<br>8.8–9.2(2H) |
| Example 59 | (59) | 53 | 277 | 2.8–3.6(8H),<br>7.4–8.0(2H),<br>8.2–8.6(2H)<br>8.8–9.2(2H) |

EXAMPLE 60

Substantially the same procedure as described in Example 3 was repeated except that 4.38 g of 2-hydroxypropylamine was used instead of ethanolamine, to thereby obtain 14.1 g of N-(2-hydroxypropyl)-8-chloro-5-quinolinesulfonamide (yield: 80%).

To 14.1 g of N-(2-hydroxypropyl)-8-chloro-5-quinolinesulfonamide were added 180 ml of pyridine and 17.87 g of paratoluenesulfonyl chloride, followed by stirring for 24 hours at a temperature of 15° C. to 20° C. After completion of the reaction, to the reaction mixture was added 450 g of ice water, followed by extraction twice each with 500 ml of dichloromethane. The dichloromethane layer was dried over anhydrous magnesium sulfate to obtain a residue. The thus obtained residue was subjected to purification by silica gel column chromatography (Wacogel C-200, 750 g; solvent: chloroform) to obtain 15.0 g of N-(2-paratoluenesulfonyloxypropyl)-8-chloro-5-quinolinesulfonamide (yield: 70%)

50 ml of a tetrahydrofuran solution containing 4.58 g of N-(2-paratoluenesulfonyloxypropyl)-8-chloro-5-quinolinesulfonamide and 4.95 g of 3,4-dimethoxyphenethylamine was heated at 70° C. for 8 hours in a sealed vessel. Then, the solvent was removed by distillation under reduced pressure to obtain a residue. The thus obtained residue was subjected to purification by silica gel column chromatography [Wacogel C-200, 200 g; solvent: a mixture of methanol and chloroform (5% methanol)] to obtain 2.37 g of N-[2-(3,4-dimethoxyphenethylamino)-2-methylethyl]-8-chloro-5-quinolinesulfonamide (60) (yield: 51%).

NMR spectrum (δ ppm)($CDCl_3$/$CD_3OD$): 0.9(3H), 2.3–3.1(7H), 3.8(6H), 6.5–6.8(3H), 7.8–8.2(3H), 8.9–9.2(2H).

IR spectrum ($cm^{-1}$): 2930, 1490, 1330, 1260, 1150, 1140, 1020, 915.

Mass spectrum (m/e): 463.

EXAMPLE 61

1.0 g of N-[2-(3,4-methylenedioxybenzylamine)ethyl]-5-isoquinolinesulfonamide (3) obtained in Example 1 was dissolved in 10 ml of methanol. To the solution was added an equal amount of aqueous hydrochloric acid, and the mixture was stirred for 10 minutes.

Then, the solvent was removed by distillation under reduced pressure to obtain a residue. The thus obtained residue was subjected to recrystallization from a mixture of methanol and ether to obtain 0.86 g of N-[2-(3,4-methylenedioxybenzylamino)ethyl]-5-isoquinolinesulfonamide hydrochloride (yield: 79%). Elementary analysis (%) of hydrochloride of compound (3)

Calculated: C: 54.09, H: 4.78, N: 9.96, Cl: 8.40

Found: C: 54.31, H: 4.52, N: 10.11, Cl: 8.62

EXAMPLES 62 AND 63

Substantially the same procedure as in Example 61 was repeated except that 1-(8-chloro-5-quinolinesulfonylaminoethyl)-4-(3,4-methylenedioxybenzyl)-homopiperazine (38) and 1-(8-chloro-5-quinolinesulfonyl)homopiperazine (54) were individually used instead of compound (3), to thereby obtain hydrochlorides of compound (38) and compound (54), respectively. Elementary analysis (%) of hydrochloride of compound (38)

Calculated: C: 53.43, H: 5.23, N: 10.38, Cl: 13.14

Found: C: 53.77, H: 5.27, N: 10.09, Cl: 13.47

Elementary analysis (%) of hydrochloride of compound (54)

Calculated: C: 46.42, H: 4.73, N: 11.60, Cl: 19.57

Found: C: 46.28, H: 4.71, N: 11.68, Cl: 19.81

APPLICATION EXAMPLE 1

Inhibitory effect on KCl-induced contraction of tracheal specimens excised from guinea pigs According to a method in which tracheal specimens excised from guinea pigs were used (Takagi and Ozawa, "Yakubutsugaku Jikken (Experiments in Pharmacology)", pp.100–102, 1960, published by Nanzando Japan; and Fujiwara and Shibata, "Yakurigaku Kiso Jikenho (Methods of Fundamental Experiments in Pharmacology)" pp.131–134, 1982, published by Kyourin, Japan), relaxing effect of sulfonamide derivatives of the present invention on bronchial smooth muscle was examined. Of compounds (1) to (69) shown herein, compounds other than acid addition salts were individually used in the form of a hydrochloride which was obtained by the same method as described in Example 61.

From male guinea pigs weighing 350 to 500 g (Hartley strain, Kuroda Junkei Dobutsu), tracheas were excised and each of the excised tracheal specimens was hung in 20 ml of a Magnus tube filled with Krebs-Henseleit solution under isotonic conditions and the solution temperature was kept at 37° C. An aqueous KCl solution was dropwise added into the Magnus tube (final KCl concentration: 20 mM) to contract the tracheal specimen. After the KCl-induced contraction became stable, each of the compounds of the present invention was dissolved in distilled water or physiological saline, and the compound solution was cumulatively added into the Magnus tube. The relaxing effect of each of the compounds of the present invention on contracted tracheal specimens was evaluated and a dose-response curve was obtained.

A dose required for relaxing KCl-induced contraction to 50%, i.e., ED50 was calculated from the dose-response curve. For comparison, the same method as described above was repeated except that aminophylline was used, to thereby determine an $ED_{50}$. The number of tracheal specimens in each group was 3.

The results are shown in Table 17.

TABLE 17

| Effect on KCl-induced contraction | |
|---|---|
| Compound No. | $ED_{50}$ (μM) |
| (1) | 7.4 |
| (2) | 15 |
| (3) | 5.2 |
| (4) | 10 |
| (5) | 28 |
| (6) | 60 |
| (7) | 70 |
| (8) | 120 |
| (9) | 30 |
| (10) | 120 |
| (11) | 125 |
| (12) | 160 |
| (13) | 28 |
| (14) | 97 |
| (15) | 110 |
| (16) | 35 |
| (17) | 71 |
| (18) | 75 |
| (19) | 125 |
| (20) | 38 |
| (21) | 128 |
| (22) | 131 |
| (23) | 163 |
| (24) | 31 |
| (25) | 105 |
| (26) | 112 |
| (27) | 86 |
| (28) | 24 |
| (29) | 22 |
| (30) | 16 |
| (31) | 13 |
| (32) | 27 |
| (33) | 24 |
| (34) | 19 |
| (35) | 18 |
| (36) | 43 |
| (37) | 48 |
| (38) | 26 |
| (39) | 31 |
| (40) | 68 |
| (41) | 78 |
| (42) | 95 |
| (43) | 106 |
| (44) | 91 |
| (45) | 84 |
| (46) | 51 |
| (47) | 60 |
| (48) | 37 |
| (49) | 46 |
| (50) | 81 |
| (51) | 85 |
| (52) | 102 |
| (53) | 120 |
| (54) | 38 |
| (55) | 45 |
| (56) | 49 |
| (57) | 57 |
| (58) | 79 |
| (59) | 90 |
| (60) | 110 |

APPLICATION EXAMPLE 2

Inhibitory effect on $PGF_{2\alpha}$-induced contraction of tracheal specimens excised from guinea pigs Tracheal specimens excised from male guinea pigs weighing 350 to 500 g (Hartley strain, Kuroda Junkei Dobutsu) were contracted in substantially the same manner as in Application Example 1 except that $PGF_{2\alpha}$ (final concentration: 1 μm) was used instead of KCl. After the contraction of the tracheal specimens became stable, each of the compounds (hydrochloride) of the present invention was dissolved in distilled water or physiological saline, and the compound solution was cumulatively added into the Magnus tube in the same manner as in Application Example 1. The relaxing effect of each of the compounds of the present invention on the contracted specimens was evaluated and a dose-response curve was obtained. The dose required for relaxing PGF2α-induced contraction to 50%, i.e., $ED_{50}$ was calculated form the dose-response curve. Of compounds 3, 4, 30, 31, 36, 38, 48, 54 and 55, which were individually used herein, compounds other than acid addition salts were used in the form of a hydrochloride which was obtained in the same manner as described in Example 61. For comparison, the same procedure as described above was repeated except that aminophylline, comparative compound (1) and comparative compound (2) were individually used instead of the compound of the present invention, to obtain an $ED_{50}$. The number of specimens in each group was 3.

The results are shown in Table 18.

APPLICATION EXAMPLE 3

Effect on trachea in vivo

According to a modified method of Konzett-Rössler method [see J. Martinez et al, Bronchial Arterial Injections, vol. 33, 295, (1961); Masaaki Takai et al, Oyo Yakuri (Applied Pharmacology), vol. 17, p.345, (1979)], effect of the compounds of the present invention on trachea in vivo was examined. Of compounds 3, 4, 30, 31, 36, 38, 48, 54 and 55, which were used herein, compounds other than acid addition salts were individually subjected to testing in the form of a hydrochloride which was obtained in the same manner as described in Example 61. Urethane was intraperitoneally administered to male guinea pigs weighing 350 to 600 g (Hartley strain, Kuroda Junkei Dobutsu) in an amount of 1.5 g/kg of body weight to anesthetize the animals. Then, cannulae were inserted into the trachea and femoral vein of each animal under urethane anesthesia and fixed. The inserted tracheal cannula was connected to a respirator for small animal (model 1683, manufactured by Harvard Co., Ltd.) and a pneumotachometer (model MHF-1200, manufactured by Nihon Kohden Corp.) through a bottle containing water, the water surface of which was adjusted to a level which is 10 cm high from the bottom, and a respiratory volume was determined.

Each of the above-mentioned compounds of the present invention was administered to guinea pigs through the femoral vein in an amount of 1 mg/kg of body weight. After 3 minutes from the administration, histamine was administered to the same guinea pigs through the femoral vein in an amount of 20 μg/kg of body weight, to thereby induce contraction of trachea and the inhibition of the histamine-induced tracheal contraction by each of the above-described compounds of the present invention was determined. For comparison, the inhibition of histamine-induced tracheal contraction by each of aminophylline, comparative compound (1) and comparative compound (2) was determined in substantially the same manner as described above. As a solvent for each compound, physiological saline was used. The number of the guinea pigs tested in each group was 3.

The results are shown in Table 19.

TABLE 18

| Compound No. | $PGF_{2\alpha}$-induced contraction $ED_{50}$ (μm) |
|---|---|
| (3) | 23 |
| (4) | 5 |
| (30) | 43 |
| (31) | 31 |
| (36) | 91 |
| (38) | 74 |
| (48) | 82 |
| (54) | 65 |
| (55) | 71 |
| Aminophylline | 200 or more |
| Comparative compound (1) | 101 |
| Comparative compound (2) | 93 |

Comparative compound (1): N-(2-aminoethyl)-N-hexyl-5-isoquinolinesulfonamide hydrochloride

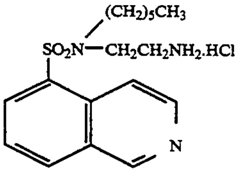

Comparative compound (2): 1-(5-isoquinolinesulfonyl)-3-aminopiperidine hydrochloride

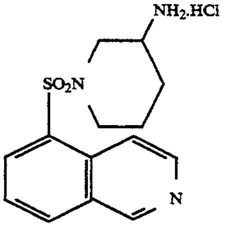

TABLE 19

| Compound No. | Inhibition of tracheal contraction (%) |
|---|---|
| (3) | 36 |
| (4) | 25 |
| (30) | 31 |
| (31) | 35 |
| (36) | 22 |
| (38) | 45 |
| (48) | 33 |
| (54) | 30 |
| (55) | 23 |
| Aminophylline | 7 |
| Comparative compound (1) | 9 |
| Comparative | 12 |

TABLE 19-continued

| Compound No. | Inhibition of tracheal contraction (%) |
| --- | --- |
| compound (2) | |

Comparative compound (1): N-(2-aminoethyl)-N-hexyl-5-isoquinolinesulfonamide hydrochloride

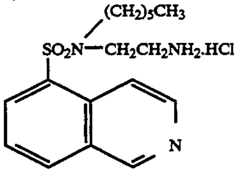

Comparative compound (2): 1-(5-isoquinolinesulfonyl)-3-aminopiperidine hydrochloride

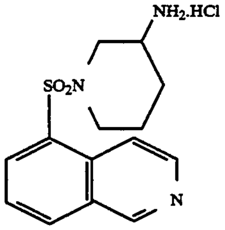

INDUSTRIAL APPLICABILITY

A pharmaceutical composition containing the novel sulfonamide derivative of the present invention or a pharmaceutically acceptable acid addition salt thereof as an active ingredient exhibits excellent bronchodilating effect, but does not exhibit adverse effect on heart and the like. In addition, the compounds of the present invention are useful as an effective medicine for prevention and treatment of respiratory diseases, such as an intractable asthma which is not relieved by the treatment of a xanthine derivative.

We claim:

1. A sulfonamide derivative represented by formula (I) or a pharmaceutically acceptable acid addition salt thereof

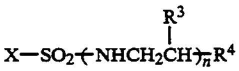

(I)

wherein X represents a quinoline residue represented by formula (II) or an isoquinoline residue represented by formula (III)

(II)

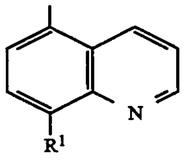

wherein $R^1$ is a hydrogen atom, a halogen atom, a lower alkyl group or a lower alkoxy group, or (III)

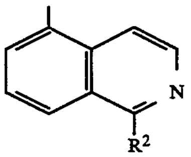

where $R^2$ is a hydrogen atom or a hydroxyl group, and wherein:

when X is quinoline residue (II), n is zero, or 1, in which, when n is zero, $R^4$ is an unsubstituted piperazinyl group or a piperazinyl group substituted by a group represented by formula IV:

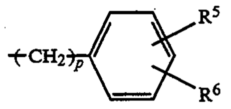

(IV)

wherein p represents an integer of from 1 to 3, and $R^5$ and $R^6$ each independently represents a hydrogen atom, a lower alkyl group, a halogen atom or a trifluoromethyl group, or $R^5$ and $R^6$ together form a methylene dioxy group; and when n is 1, $R^3$ is a hydrogen atom or a lower alkyl group and $R^4$ is an unsubstituted piperazinyl group or a piperazinyl group substituted by a group represented by formula IV; and when X is isoquinoline residue (III), n is 1, in which, $R^3$ is a hydrogen atom or a lower alkyl group and $R^4$ is an unsubstituted piperazinyl group or a piperazinyl group substituted by a group represented by formula IV, said piperazinyl group being bonded at the nitrogen atom thereof.

2. The sulfonamide derivative or pharmaceutically acceptable acid addition salt thereof according to claim 1, wherein X represents a quinoline residue represented by formula (II) where $R^1$ is a halogen atom or a lower alkoxy group.

3. The sulfonamide derivative or pharmaceutically acceptable acid addition salt thereof according to claim 2, wherein n is 1 and $R^3$ is a hydrogen atom.

4. The sulfonamide derivative or pharmaceutically acceptable acid addition salt thereof according to claim 1, wherein X represents an isoquinoline residue represented by formula (III), and $R^3$ is a hydrogen atom.

5. The sulfonamide derivative or pharmaceutically acceptable acid addition salt thereof according to any one of claims 1 and 4, wherein X represents an isoquinoline residue represented by formula (III) where $R^2$ is a hydrogen atom.

6. The sulfonamide derivative or pharmaceutically acceptable acid addition salt thereof according to any one of claims 1 and 4, wherein X represents an isoquinoline residue represented by formula (III) where $R^2$ is a hydroxyl group.

7. A pharmaceutical composition comprising the sulfonamide derivative or pharmaceutically acceptable acid addition salt thereof according to claim 1, and at least one pharmaceutically acceptable carrier or diluent.

8. A pharmaceutical composition comprising the sulfonamide derivative or pharmaceutically acceptable acid addition salt thereof according to claim 2, and at least one pharmaceutically acceptable carrier or diluent.

9. A pharmaceutical composition comprising the sulfonamide derivative or pharmaceutically acceptable acid addition salt thereof according to claim 3, and at least one pharmaceutically acceptable carrier or diluent.

10. A pharmaceutical composition comprising the sulfonamide derivative or pharmaceutically acceptable acid addition salt thereof according to claim 4, and at least one pharmaceutically acceptable carrier or diluent.

11. A pharmaceutical composition comprising the sulfonamide derivative or pharmaceutically acceptable acid addition salt thereof according to claim 5, and at least one pharmaceutically acceptable carrier or diluent.

12. A pharmaceutical composition comprising the sulfonamide derivative or pharmaceutically acceptable acid addition salt thereof according to claim 6, and at least one pharmaceutically acceptable carrier or diluent.

13. The sulfonamide derivative of claim 1, wherein said derivative is 1-(5-isoquinoline-sulfonylaminoethyl)-4-(3,4-methylenedioxybenzyl)piperazine.

* * * * *

UNITED STATES PATENT AND TRADEMARK OFFICE

CERTIFICATE OF CORRECTION

PATENT NO. : 5,340,811

DATED : August 23, 1994

INVENTOR(S) : A. Kajihara et al.

It is certified that error appears in the above-indentified patent and that said Letters Patent is hereby corrected as shown below:

On the title page :
[22] Filed: Jul. 17, 1990 should be --[22] PCT Filed: Mar. 8, 1990--;

Please insert "[86] PCT No.: PCT/JP90/00303

§ 371 Date: Jul. 17, 1990

§ 102(e) Date: Jul. 17, 1990

[87] PCT Pub. No.: WO91/13875

PCT Pub. Date: Sep. 19, 1991"

Signed and Sealed this

Thirteenth Day of June, 1995

Attest:

BRUCE LEHMAN

*Attesting Officer* *Commissioner of Patents and Trademarks*